(12) United States Patent
Lombardía et al.

(10) Patent No.: US 11,001,799 B2
(45) Date of Patent: May 11, 2021

(54) BIOLOGICAL DISINFECTION OR STERILIZATION INDICATOR

(71) Applicant: TERRAGENE LLC, Spring, TX (US)

(72) Inventors: Esteban Lombardía, Pueblo Esther (AR); Adrián Jesús Rovetto, Rosario (AR)

(73) Assignee: TERRAGENE LLC, Spring, TX (US)

( * ) Notice: Subject to any disclaimer, the term of this patent is extended or adjusted under 35 U.S.C. 154(b) by 182 days.

(21) Appl. No.: 16/164,418

(22) Filed: Oct. 18, 2018

(65) Prior Publication Data

US 2020/0123492 A1 Apr. 23, 2020

(51) Int. Cl.
*C12Q 1/22* (2006.01)
*C12M 1/12* (2006.01)
*C12M 1/00* (2006.01)
*C12M 3/00* (2006.01)
*G01N 21/64* (2006.01)

(52) U.S. Cl.
CPC ............ *C12M 37/06* (2013.01); *C12M 23/06* (2013.01); *C12M 23/28* (2013.01); *C12M 23/38* (2013.01); *C12M 23/54* (2013.01); *C12M 25/14* (2013.01); *C12Q 1/22* (2013.01); *G01N 21/6428* (2013.01); *G01N 2021/6439* (2013.01)

(58) Field of Classification Search
CPC combination set(s) only.
See application file for complete search history.

(56) References Cited

U.S. PATENT DOCUMENTS

| 5,770,393 | A | 6/1998 | Dalmasso et al. |
| 5,856,118 | A | 1/1999 | Dalmasso et al. |
| 7,326,562 | B2 | 2/2008 | Felkner et al. |
| 8,765,398 | B2 | 7/2014 | Dalmasso |
| 8,969,029 | B2 | 3/2015 | Chandrapati et al. |
| 8,975,067 | B2 | 3/2015 | Foltz et al. |

FOREIGN PATENT DOCUMENTS

| EP | 2654808 A1 | 10/2013 |
| WO | WO-2014149379 A1 | 9/2014 |

*Primary Examiner* — Heidi Reese
(74) *Attorney, Agent, or Firm* — Muncy, Geissler, Olds & Lowe, P.C.

(57) ABSTRACT

A biological indicator for testing the efficacy of sterilization or disinfection processes of closed environments or confined spaces, the biological indicator comprising a carrier; biological material supported on or embedded in the carrier; and a carrier container comprising a body and a cap. The carrier is fixed within an inner space of the cap, the cap being able to be placed in an open position completely exposing the carrier and the biological material to the closed environment or confined space to be disinfected. A method for determine the efficacy of a process of sterilization or disinfection of closed environments or confined spaces, preferably by means of an enzyme and a fluorescence compound, using said biological indicator.

18 Claims, 7 Drawing Sheets

BIOLOGICAL DISINFECTION OR STERILIZATION INDICATOR

FIELD OF THE INVENTION

The present invention relates to the field of disinfection or sterilization of closed environments or confined spaces by means of gas, plasma, steam, spray, chemical vapors or chemical fogs. More particularly, the invention relates to a biological indicator for monitoring and determining the efficacy of disinfection or sterilization processes.

BACKGROUND OF THE INVENTION

There is extensive bibliography on sterilization devices, processes and methods to test their efficacy. "Sterilization" is understood as the complete elimination of microorganisms, including structures such as viruses, bacteria and their spores. The devices available on the market are aimed at determining the efficiency of sterilization. Sterilization is mainly used in decontamination processes on instruments and materials for medical use, as well as on equipment used in the pharmaceutical industry and the food industry among others. Determining sterility is vital for various fields, such as those of health care and aerospace science and technology, to mention a few. In general, these sterilization processes are based on cycles that consist in introducing the material to be sterilized in a chamber and subjecting it to a selected sterilization agent. Among these sterilization agents, the following can be mentioned: steam, hydrogen peroxide, formaldehyde, ozone, tetrasilver tetraoxide and ethylene oxide. These processes include a vacuum stage in which the air from the chamber is extracted, so that said chamber is subsequently filled with the sterilizing agent. This step enables the sterilizing agent to penetrate into the most hidden spaces of the materials to be sterilized. Consequently, most devices used to measure sterilization efficacy contain biological samples hidden or with interferences in the pathway of the sterilization agent. This feature, added to the fact that the biological indicators generally include as the biological sample the most resistant microorganism to the sterilization agents, enhances the accuracy of the obtained results.

Biological and chemical indicators used to determine the efficacy of sterilization are well known in the art. Regarding conventional biological indicators, a test organism which is many times more resistant to sterilization process than most organisms likely to be present due to natural contamination, is coated on a carrier and placed in a sterilizer together with the items to be subjected to sterilization. When the cycle of sterilization is complete, the carrier is incubated in a nutrient medium to determine if any of the test organisms survived the procedure of sterilization.

It is also known that when an enzyme is subjected to sterilization conditions, sufficient to decrease the population of test microorganisms by about 6 logs, no residual activity remains. However, the biological indicator has a residual signal, which is equal to the "background". When the enzyme is subjected to inappropriate sterilization conditions, sufficient to decrease the population of test microorganisms only in the range of 1-6 logs, the enzyme has an activity greater than the background. This activity is measured as the result of the reaction of the enzyme with a substrate system. The enzyme substrate system is a substance or mixture of substances, which interacts with the enzyme to produce a detectable enzyme-modified product, e.g. a fluorescent or colored product. Thus the enzyme activity is measured by the amount of detectable product. Generally, the selected enzymes have sufficient activity, following sterilization conditions insufficient to decrease the population of the test microorganism by 6 logs, to react with the substrate and produce a detectable amount of product preferably within two hours or less.

Usually, the enzyme activity is 2-10% greater than background after sterilization conditions that are insufficient to decrease the microorganism population by 6 logs.

When a microorganism is used as the source of active enzyme, the monitoring process may include a step of incubating the microorganism, following the completion of the sterilization cycle, with an aqueous nutrient medium. The inclusion of this step allows confirming by conventional techniques whether the sterilization conditions had been sufficient to kill all the microorganisms in the biological indicator, showing that the sterilization conditions had been sufficient to sterilize all the items inside the sterilizer. If growth of the microorganism is used in a conventional manner to confirm the results of the enzyme test, the microorganism should be one which is conventionally used to monitor sterilization conditions. These conventionally used microorganisms are generally many times more resistant to the sterilization process being employed, than most organisms present in natural contamination. Bacterial spores are recognized as the most resistant microbial form of life. Spores from *Bacillus* and *Clostridia* species are most commonly used to monitor sterilization processes utilizing saturated steam, dry heat, gamma irradiation, hydrogen peroxide and ethylene oxide.

It is known that a plurality of enzymes and/or microorganism species could be used together. A single biological material indicator may contain several species of microorganisms, for instance one species being resistant to heat, a second species being resistant to gaseous sterilizing agent and a third species being resistant to radiation.

Several technologies to determine the efficacy of sterilization, have been disclosed in patent documents such as: WO 2014/149379 U.S. Pat. Nos. 7,326,562, 5,770,393, EP 2654808, U.S. Pat. No. 8,975,067. Said patent documents describe containers of biological indicators that interfere in the pathway of the sterilizing agent; i.e. they require vacuum or low pressure in the sterilization chamber for the sterilizing agent to penetrate and act more efficiently; therefore, they are not suitable for the assessment of disinfection of rooms, closed environments and confined spaces. Biological indicators for test disinfection of rooms, closed environments and confined spaces need a special physical design.

On the other hand, biological indicators have been disclosed to contribute to the assessment of decontamination in open or confined spaces such as in U.S. Pat. Nos. 5,856,118 and 8,765,398, but they do not guarantee sterility and they require manipulation and transfer for their development, which may result in "false positive" readings. In addition, the disclosed indicators do not include a culture medium, which must be supplied separately from the system. Complex mechanisms that might meet the requirements for determining the efficacy of disinfection have also been disclosed, such as those described in U.S. Pat. No. 8,969,029, which are expensive devices and require dedicated incubators.

The disinfection of rooms such as isolated chambers, operating rooms, food processing and pharmaceutical manufacturing areas is widely used nowadays, and there is a need of low-cost systems designed for a rapid determination of disinfection efficacy in the state of the art.

The present invention addresses this need by providing a biological indicator specially designed for a rapid determination of the efficacy of disinfection or sterilization processes in closed environments and confined spaces.

BRIEF DESCRIPTION OF THE INVENTION

The biological indicator of the present invention has been specially designed for a rapid determination of the efficacy of the disinfection processes in confined spaces and it can be placed on any horizontal surfaces such as counters, shelves, furniture, floors of rooms or other closed environments to be disinfected. Once disinfection is performed, the biological indicator of the present invention is typically developed in about 30 to 90 minutes, usually one hour, indicating if the disinfection process has been successful or not.

Therefore, in a first aspect the present invention provides "semi-self-contained" or "self-contained" biological indicator devices for indicating the disinfection or sterilization efficacy of closed environments or confined spaces sterilization or disinfection. The device of the invention enables the evaluation of disinfection processes in closed environments or confined spaces, such as rooms, by means of a simple operation with minimum manipulation and very low cost due to the simplicity of its structure.

The biological indicator of this first aspect of the present invention, comprises:
 a) a carrier;
 b) biological material supported on or embedded in the carrier; and
 c) a carrier container comprising a body and a cap;
  wherein the carrier is fixed within an inner space of the cap, the cap being able to be placed in an open position completely exposing the carrier and the biological material to the closed environment or confined space to be disinfected.

Therefore, when using the indicator, the carrier is exposed to a sterilizing agent in the absence of vacuum, which means that the present invention does not require producing vacuum in the closed environment or confined space that is been disinfected.

In an embodiment of this first aspect of the invention, the biological indicator further comprises a cap holder for keeping the cap in the open position and exposing the carrier and the biological material to the close environment or confines space to be disinfected.

In another embodiment of this first aspect of the invention, the cap comprises an external wall with a flat portion that enables the cap placement on a flat surface in the open position.

In preferred embodiments of this first aspect of the invention the carrier is made of a material selected from the group consisting of steel, polymeric materials, thermoplastic materials, synthetic or natural fibers, cellulose, vitreous materials and combinations thereof.

In a more preferred embodiment of this first aspect of the invention, the carrier comprises the biological material adhered to its surface.

In yet a preferred embodiment of this first aspect of the present invention, the biological material is selected from the group consisting of bacteria, spores, enzymes and combinations thereof.

In a more preferred embodiment of this first aspect of the present invention, the biological material is selected from the group consisting of non-pathogenic *Bacillus* spp., *Geobacillus* spp., *Clostridium* spp., *Neurospora* spp., *Candida* spp. and combinations thereof. More preferably *Bacillus subtilis*, *Bacillus atrophaeus*, *Bacillus pumilus*, *Geobacillus stearothermophilus* and most preferably *Bacillus subtilis* ATCC35021, *Geobacillus stearothermophilus* ATCC7953, *Bacillus atrophaeus* ATCC9372, and *Bacillus pumilus* ATCC27142.

In another embodiment of this first aspect of the present invention, the indicator device further comprises a growth medium container that contains a growth medium for the biological material.

In a preferred embodiment of this first aspect of the present invention, the biological indicator is semi self-contained and the growth medium is contained within a collapsible ampoule which is placed within the growth medium container. Preferably, the collapsible ampoule is a container comprising a breakable membrane.

In a more preferred embodiment of this first aspect of the present invention, the container that contains the growth medium comprises an air-tight cap or a cap with a biological barrier.

In preferred embodiments of this first aspect of the invention, the growth medium comprises nutrients; fluorescent components which react in the presence of active enzymes producing a fluorescence signal; and a chemical indicator to produce a color change with the growth of microorganisms.

In yet preferred embodiments of this first aspect of the invention, the nutrients are selected from the group consisting of peptone, yeast extract, amino acids, meat extract, casein digest, tryptone, peptone from casein, soybean protein digest and combinations thereof.

In an embodiment of this first aspect of the present invention, the carrier essentially consists of the external surface of an ampoule, preferably a collapsible ampoule, that contains the growth medium. Preferably, the ampoule is structurally linked to the internal part of the carrier container. More preferably, the ampoule is structurally linked to the inner space of the cap of the carrier container.

In another embodiment of this first aspect of the present invention, the carrier essentially consist of the inner surface of the carrier container.

In a preferred embodiment of the present invention, said biological indicator is semi self-contained and comprises a second container comprising a collapsible ampoule containing the growth medium; and the carrier comprises a sheet containing the biological material adhered to its surface, where said biological material is selected from the group comprising bacteria, spores and enzymes; wherein the carrier is linked to the inner space of the cap of the carrier container which, when opened, enables the positioning of the carrier completely exposed to the closed environment or confined space to be disinfected, fitted into a cap-holder, into which said cap fits.

In a second aspect, the present invention provides a method to determine the efficacy of a process of sterilization or disinfection of closed environments or confined spaces, preferably by means of an enzyme and a fluorescence compound, as part of the biological material in the biological indicator of the first aspect of the invention, the method comprising the following steps:
 i. removing the cap of the container of the biological indicator, wherein said cap comprises the biological material carrier fixed within its inner space;
 ii. inserting the cap of step i. in a cap-holder, leaving the biological material carrier completely exposed to the closed environment or confined space to be sterilized or disinfected;

iii. providing a sterilizing agent into the closed environment or confined space to be sterilized or disinfected;
iv. on completion of the disinfection process, putting into contact the biological material carrier and the growth medium, e.g. by breaking an ampoule containing the growth medium;
v. incubating the biological indicator by inserting the same into a device capable of keeping an appropriate temperature, preferably at 60° C. and irradiating with LED light at 375 nm, and recording the fluorescence emission of the container;
vi. sensing fluorescence after 10 minutes and during the first hour of incubation, preferably between 400 to 540 nm;
vii. determining the efficacy of the sterilization or disinfection process according to the following criterion: if the enzyme has not been inactivated, it reacts with said fluorescence compound and fluorescence is detected; therefore it is concluded that the sterilization or disinfection process failed.

In preferred embodiment of this second aspect of the invention, following step iv. and as a step iv-a, the method comprises removing the cap from the cap-holder and closing the container that contains the broken ampoule by using said cap, which contains the biological material carrier, when the biological indicator is a semi self-contained biological indicator.

In preferred embodiment of this second aspect of the invention, the biological material is selected from the group consisting of bacteria, spores, enzymes and the combinations thereof. Preferably, said biological material is selected from the group consisting of non-pathogenic *Bacillus* spp., *Geobacillus* spp., *Clostridium* spp., *Neurospora* spp., *Candida* spp. and combinations thereof. More preferably *Bacillus subtilis*, *Bacillus atrophaeus*, *Bacillus pumilus*, and *Geobacillus stearothermophilus* and most preferably *Bacillus subtilis* ATCC35021, *Geobacillus stearothermophilus* ATCC7953, *Bacillus atrophaeus* ATCC9372, *Bacillus pumilus* ATCC27142 and combinations thereof. Other species like *Clostridium* spp., *Neurospora* spp., *Candida* spp. could also be used. On the other hand, a purified enzyme from any of the organisms is also a possible option.

BRIEF DESCRIPTION OF DRAWINGS

The appended figures are schematic views of preferred embodiments of the present invention. They are illustrative and not intended to limit the scope of claims.

DETAILED DESCRIPTION OF THE INVENTION

The present invention provides semi self-contained or self-contained indicators of the efficacy of rooms, closed environments and confined spaces sterilization or disinfection. It enables the evaluation of said sterilization or disinfection processes by means of a simple operation with minimum manipulation and very low cost due to the simplicity of its structure.

The present invention provides a biological indicator to determine the efficacy of sterilization or disinfection of rooms, closed environments and confined spaces. Usually, said sterilization or disinfection are performed by a sterilizing agent such as peracetic acid, OPA (Ortho-phthalaldehyde), formaldehyde, glutaraldehyde, ethylene oxide, hydrogen peroxide, tetrasilver tetraoxide, ozone, radiation, nitrogen dioxide, hydrogen peroxide gas plasma, steam and dry heat among other disinfection methods.

As used herein, the term "biological indicator" refers to a device for determining the efficacy of sterilization or disinfection processes for rooms, closed environments or confined space. This device comprises a carrier, biological material, a growth medium confined and at least one container wherein said carrier comprises a support surface for said biological material; said carrier is linked to the inner space of a cap, that could be placed completely exposed to the confined space to be disinfected; and said growth medium is confined to a collapsible ampoule.

As used herein the term "confined space" or "closed environment" refer to, inter alia, indoor spaces, rooms in general, preferably operating rooms and hospital rooms, isolated technology spaces, laboratory hoods, food manufacturing areas, pharmaceutical manufacturing and laboratory areas.

The term "carrier" as used herein refers to a material that supports biological material.

The term "biological material" as used herein refers to microorganisms, spores or enzymes that exhibit high resistance to a sterilizing agent and are useful to indicate if a disinfection process is successful. The biological material is exposed to a sterilization or disinfection process and if it is not inactivated, the sterilization or disinfection failed. In the present invention, the biological material may be selected from the group comprising the following species and their combinations: caprylate esterase, lipase, alpha-D-glucosidase, beta-D-glucosidase, alkaline phosphatase, butyrate esterase, myristate lipase, leucine aminopeptidase, valine aminopeptidase, beta-D-glucuronidase, alpha-D-glucuronidase, chymotrypsin, phenylalanine aminopeptidase, phosphohydrolase, alpha-D-galactosidase, beta-D-galactosidase, alpha-L-arabinofuranosidase, N-acetyl-beta-glucosaminidase, N-acetyl-alpha-glucosaminidase, acid phosphatase, beta-D-cellobiosidase, alanine aminopeptidase, proline aminopeptidase, tyrosine aminopeptidase, and a fatty acid esterase, derived from spore-forming microorganisms.

The preferred biological material for the present invention are several spore-forming microorganisms like *Bacillus subtilis* spp., *Geobacillus stearothermophilus* spp., *Bacillus atrophaeus* spp., *Bacillus pumilus* spp. and species like *Clostridium* spp., *Neurospora* spp. and *Candida* spp, more preferably *Bacillus subtilis* ATCC35021, *Geobacillus stearothermophilus* ATCC7953, *Bacillus atrophaeus* ATCC9372, *Bacillus pumilus* ATCC27142

The enzymes useful in the present invention are extracellular and intracellular enzymes, whose activity correlates with the viability of at least one microorganism commonly used to monitor sterilization efficacy. The enzyme activity could be used to predict the future growth of microorganisms. The enzyme must be one which following a disinfection process, which is sublethal to the microorganism, remains sufficiently active to react with a fluorescence compound.

The term "chemical indicator" as used herein refers to a compound that presents color changes in case the disinfection process was not successful. This color change is due to a pH variation because of a microbial growth after incubation at adequate temperature and time.

The suitable chemical indicator for the present invention may be selected from the group comprising: 5-bromo-4-chloro-3-indolyl derivatives including 5-bromo-6-chloro-3-indolyl acetate, 5-bromo-4-chloro-3-indolyl acetate, 5-bromo-4-chloro-3-indoxyl-beta-D-galactopyranoside, 5-bromo-4-chloro-3-indolyl-1,3-diacetate, 5-bromo-4-chloro-3-indolyl-beta-D-fucopyranoside, 5-bromo-4-chloro-3-indolyl-beta-D-glucopyranoside, 5-bromo-4-chloro-3-indolyl-beta-D-glucuronic acid, 5-bromo-4-chloro-3-indolyl phosphate, and 5-bromo-4-chloro-3-indolyl sulfate, diethyl-p-nitrophenyl phosphate; di-p-nitrophenyl phosphate; p-nitrophenyl-2-acetamido-2-deoxy-3-O-beta-galactopyranosyl-beta-glucopyranoside; p-nitrophenyl-2-acetamido-2-deoxy-beta-glucopyranoside; p-nitrophenyl acetate; p-nitrophenyl-N-acetyl-beta-D-glucosaminide; p-nitrophenyl-beta-D-N, N'-diacetylchitobioside; p-nitrophenyl-alpha-glucopyranoside; p-nitrophenyl-alpha-maltoside; p-nitrophenyl-beta-maltoside; p-nitrophenyl-alpha-mannopyranoside; p-nitrophenyl-beta-mannopyranoside; p-nitrophenyl myristate; p-nitrophenyl palmitate; p-nitrophenyl phosphate; bis(p-nitrophenyl) phosphate; tris(p-nitrophenyl)phosphate; p-nitrophenyl-beta-glucopyranoside; p-nitrophenyl-beta-glucuronide; alpha-p-nitrophenylglycerine; p-nitrophenyl-alpha-rhamnopyranoside; p-nitrophenyl stearate; p-nitrophenyl sulfate; p-nitrophenyl-2,3,4,6-tetra-O-acetyl-beta-glucosaminide; p-nitrophenyl thymidine monophosphate; p-nitrophenyl-2, 3,4-tri-O-acetyl-beta-glucuronic acid methyl ester; p-nitrophenyl valerate, o-nitrophenyl acetate, o-nitrophenyl-beta-glucoside and o-nitrophenyl-beta-D-glucopyranoside. Other particularly nitrophenyl derivatives include nitrophenyl-beta-fucopyranoside; nitrophenyl-alpha-galactopyranoside; nitrophenyl-beta-galactopyranoside; nitrophenyl butyrate; nitrophenyl caprate; nitrophenyl caproate; nitrophenyl caprylate; nitrophenyl laurate, indoxyl-acetate; indoxyl beta-D-glucoside; 3-indoxyl sulfate; 3-indoxyl phosphate, phenolphthalein dibutyrate; phenolphthalein diphosphate; phenolphthalein disulfate; phenolphthalein glucuronic acid; phenolphthalein mono-beta-glucosiduronic acid; phenolphthalein mono-beta-glucuronic acid; phenolphthalein monophosphate.

The fluorescent components that may be used in the present invention are compounds which, when reacting with an enzyme, yields a product which exhibits fluorescence, detectable in very low concentrations. The fluorescent component could be selected from the group comprising: 4-methylumbelliferyl derivatives; derivatives of 7-amido-4-methylcoumarin; diacetylfluorescein derivatives; fluorescamine; 4-methylumbelliferyl-2-acetamido-4, 6-0-benzylidene-2-deoxy-beta-D-glucopyranoside; 4-methylumbelliferyl acetate; 4-methylumbelliferyl-N-acetyl-beta-D-galactosaminide; 4-methylumbelliferyl-N-acetyl-alpha-D-glucosaminide; 4-methylumbelliferyl-N-acetyl-beta-D-glucosaminide; 2'-(4-methylumbelliferyl)-alpha-D-N-acetyl neuraminic acid; 4-methylumbelliferyl alpha-L-arabinofuranoside; 4-methylumbelliferyl alpha-L-arabinoside; 4-methylumbelliferyl butyrate; 4-methylumbelliferyl beta-D-cellobioside; methylumbelliferyl beta-D-N, N'-diacetyl chitobioside; 4-methylumbelliferyl elaidate; 4-methylumbelliferyl beta-D-fucoside; 4-methylumbelliferyl alpha-L-fucoside; 4-methylumbelliferyl beta-L-fucoside; 4-methylumbelliferyl alpha-D-galactoside; 4-methylumbelliferyl beta-D-galactoside; 4-methylumbelliferyl alpha-D-glucoside; 4-methylumbelliferyl beta-D-glucoside; 4-methylumbelliferyl beta-D-glucuronide; 4-methylumbelliferyl p-guanidinobenzoate; 4-methylumbelliferyl heptanoate; 4-methylumbelliferyl alpha-D-mannopyranoside; 4-methylumbelliferyl beta-D-mannopyranoside; 4-methylumbelliferyl oleate; 4-methylumbelliferyl palmitate; 4-methylumbelliferyl phosphate; 4-methylumbelliteryl propionate; 4-methylumbelliferyl stearate; 4-methylumbelliferyl sulfate; 4-methylumbelliferyl beta-D-N, N', N'''-triacetylchitotriose; 40-methylumbelliferyl 2,3,5-tri-o-benzoyl-alpha-L-arabinofuranoside; 4-methylumbelliferyl-p-trimethylammonium cinnamate chloride; and 4-methylumbelliferyl beta-D-xyloside; 7-amido-4-methylcoumarin derivatives include: L-alanine-7-amido-4-methylcoumarin; L-proline-7-amido-4-methylcoumarin; L-tyrosine-7-amido-4-methylcoumarin; L-leucine-7-amido-4-methylcoumarin; L-phenylalanine-7-amido-4-methylcoumarin; and 7-glutarylphenylalanine-7-amido-4-methylcoumarin; N-t-BOC-Ile-Glu-Gly-Arg 7-amido-4-methyl coumarin; N-t-BOC-Leu-Ser-Thr-Arg 7-amido-4-methylcoumarin; N-CBZ-Phe-Arg 7-amido-4-methylcoumarin; Pro-Phe-Arg 7-amido-4-methylcoumarin;

N-t-BOC-Val-Pro-Arg 7-amido-4-methylcoumarin; and N-glutaryl-Gly-Arg 7-amido-4-methylcoumarin; fluorescein diacetate, fluorescein di-(beta-D-galactopyranoside), fluorescein dilaurate.

As used herein, the term "growth medium" refers to a mix between well-known microorganism nutrients such as proteins, carbohydrates, yeast extracts, etc., fluorescent components and a chemical indicator. This medium is adequate to develop a fluorescence signal when enzymes, which have not been affected by disinfection process, interact with a fluorescent component (fluorophore). This medium also allows the growth of spores surviving disinfection process, changing its color in 48 hours of incubation.

The term "reaction medium" as used herein refers to a mix between well-known fluorescent and non-fluorescent components and a colorant compound. This medium is adequate to develop a fluorescence signal when enzymes, which have not been affected by disinfection process, interact with a fluorescent component (fluorophore).

In the present application, the terms "sterilization" and "disinfection" are used interchangeably for designating a process for killing microorganisms in objects or surfaces.

As used herein, the term "sterilizing agent" refers to compounds that are used to kill microorganism (including virus and deactivation of enzymes) in the form of gas, spray, liquid or plasma, such as, inter alia, peracetic acid, OPA (Ortho-phthalaldehyde), formaldehyde, glutaraldehyde, ethylene oxide, hydrogen peroxide, tetrasilver tetraoxide, ozone, radiation, nitrogen dioxide, hydrogen peroxide gas plasma, steam and dry heat and combinations thereof or other disinfection methods.

The term "self-contained" applied to a biological indicator according to the present invention is intended to mean that the biological indicator of the invention is completely contained in a single container, encompassing the carrier of the biological material as well as the growth medium.

The term "semi self-contained" applied to a biological indicator according to the present invention is intended to mean that the biological indicator of the invention is contained in two containers: a first one containing the carrier with the biological material and a second one containing the growth medium. It is then required that, after the disinfection process, the carrier with biological material in the cap of the first container be introduced into the second container with the growth medium to proceed to incubation, which will determine the efficacy of the disinfection process.

A "holder" in a preferred embodiment of the invention, is the cap of a first container that comprises means to hold the carrier in its inner space.

A "cap-holder", according to the present invention is a device that supports a cap. In a preferred embodiment, it is a solid piece with several holes into which the cap can fit. It is a base that presents spaces where the cap that contain the carrier fit. In a preferred embodiment of the invention, said cap-holder is a solid base with cylindrical holes where the caps of the containers fit, enabling the carrier of the biological medium supported in the internal part of said cap to fit perpendicularly into the supporting surface, in a safe manner, assuring the complete exposure of the carrier and therefore, of the biological indicator. The "cap-holder" could also be used to support the tube or others biological indicator accessories parts.

This invention uses biological material constituted, preferably, by bacterial spores of *Bacillus subtilis* ATCC35021, *Geobacillus stearothermophilus* ATCC7953, *Bacillus atrophaeus* ATCC9372, *Bacillus pumilus* ATCC27142, among others and combinations thereof, or enzymes or combinations of spores and enzymes. This biological material is placed, in one preferred embodiment of the invention, on a laminar carrier which presents a surface of stainless steel, steels and their alloys, polypropylene, polyethylene, polyester, glass, quartz among other possibilities. The invention also comprises a growth medium which enables the germination and/or growth of spores and enzyme catalytic activity or enables the detection of the metabolic activity of spores or microorganisms or enzymatic activity of spores or enables the detection of metabolites or enzymes produced by spores during their growth or germination.

The present invention provides, in a preferred embodiment, a semi self-contained biological indicator with two containers: a first one, which contains the biological material-spores or enzymes or the combinations thereof- and a second one which contains the growth medium. These two different containers are compatible in their parts, allowing the cap of one of them to fit and be fastened on top of the other. The cap and the container enable both parts to be kept under sterile conditions when it is closed. In the process of room and confined space disinfection, the first container with the biological material carrier is opened, and it is exposed to the room or confined space to be disinfected in the absence of space blocking or surfaces interposed between said biological material and the disinfection agent. In a preferred embodiment of the present invention, the carrier of the biological material is a sheet adhered to the internal part of the cap of the first container, while the growth medium is contained in the second container. The growth medium, in a preferred embodiment of the present invention, is maintained under sterile conditions or in a plastic or glass ampoule capable of releasing its content by lateral pressure from the walls of the second container, or by pressure of the cap. Once the carrier with biological material is exposed to the sterilization or disinfection process, the cap containing said carrier is introduced into the second container which has the growth medium. Thus, both the biological material and the growth medium come into contact to proceed to incubation.

The present invention allows easy manipulation and rapid and bacteriologically safe assembly to make the biological material come into contact with its growth medium.

As it is known in the art such growth medium is constituted by nutrients and fluorescent components, which react in the presence of active enzymes to produce a fluorescence signal and chemical indicators to cause color changes with the growth of microorganisms.

Another object of the present invention is a procedure to determine the efficacy of confined spaces disinfection processes comprising the following steps:

a) removing the cap of the container of the biological indicator, wherein said cap comprises a holder for said biological material carrier in its inner space;

b) inserting the cap of step a) in a cap-holder, leaving said biological material carrier completely exposed to the confined space to be disinfected;

c) proceeding with sterilization or disinfection process using a sterilizing agent;

d) on completion of the disinfection process, putting into contact the biological material carrier and the growth medium, breaking the ampoule containing the growth medium;

e) incubating the biological indicator by inserting the biological indicator into a device capable of keeping the appropriate temperature and record the fluorescence emission from the container. In this way the failure of the disinfection cycle can be detected in the following different ways:

by emitting fluorescence from the container, with a light at a frequency appropriate for the identification of the compound that is formed by the catalytic activity of an enzyme or protein and a fluorescence compound;
by changing the color of the growth medium; or
through the two options described above
where in this step e) the biological material is incubated at a suitable temperature and illuminated with light at a suitable frequency for the identification of fluorescence of a compound released when enzyme react with the fluorescence compound. Throughout an incubation period of an hour, fluorescence is sensed between 400 and 540 nm; if the enzyme has not been inactivated, said released compound from reaction of said enzyme and said fluorescence compound is detected in a time of fluorescence between 30 and 90 minutes, preferably less than 60 minutes and it is concluded that the disinfection processes failed.

f) if during the analysis period, no fluorescence signal is detected, or the color of the culture medium remains unchanged, it is concluded that the disinfection process has been successful.

The process of the invention with a preferred embodiment comprising a semi self-contained biological indicator with two containers comprises the following steps:

a) removing the cap of the first container of the biological indicator, wherein said cap presents self-contained positioning support for said biological material carrier;

b) inserting the cap of step a) in a cap-holder, leaving said biological material carrier completely exposed to the room or confined space to be disinfected;

c) proceeding with disinfection using a sterilizing agent;

d) on completion of disinfection, opening and pressing a second container to break the ampoule containing the growth medium, and discarding the cap;

e) removing the cap of the first container from the cap-holder and closing the second container using the cap of the first container which contains the biological material carrier, thus causing the biological material and the growth medium to come into contact;

f) incubating the second container, closed with the cap of the first container, at a suitable temperature, preferably between 36° C. and 60° C., and irradiating with light at a suitable frequency, preferably between 300 and 400 nm, for the identification of fluorescence;

g) sensing fluorescence between 400 and 540 nm during the first hour of incubation; if the enzyme has not been inactivated, said enzyme reacts with said fluorescence compound and fluorescence is detected and it is concluded that the disinfection processes failed;

h) leaving the tube on the incubator for other 24-48 h and checking the color change of the culture medium. If after the incubation the color has changed, it could also be concluded that the disinfection processes failed.

EXAMPLES

The invention will be described in more detail by means of the following examples, that should not be construed as limiting the invention. The scope of the present invention is limited only by the claims, and numerous alternatives, modifications, and equivalents thereof would be apparent for a person skilled in the art from the teachings herein. Numerous specific details are set forth in the following description in order to provide a thorough understanding. These details are provided for the purpose of example and the described techniques may be practiced according to the claims without some or all of these specific details. For clarity, technical material that is known in the technical fields related to the examples has not been described in detail to avoid unnecessarily obscuring the description.

The Examples will make reference to FIGS. 1 to 12, when necessary, for a full understanding of the invention.

General Spore Preparation Method

All spores assayed in the examples below, were produced in TSA agar plates and grown at their required temperature (60° C. for *G. stearothermophilus* and 37° C. for *B. subtilis, B. atrophaeus* and *B. pumilus*). Prior to be harvested, they were washed two times with sterilized distilled water at 4-8° C. The spores suspensions were centrifuged at 6000 RPM for 30 minutes and resuspended in the necessary volume of clean distilled water to obtain a population of approximately 1.109 UFC/ml.

Example 1. Manufacturing a Semi Self-Contained Biological Indicator of the Invention Referring to FIGS. 1 and 2, a semi self-contained biological indicator for determining the efficacy of sterilization or disinfection processes for closed environments and confined spaces, consisting of a first and a second container was manufactured. The containers are respective tubes 2 and 6 with respective caps 1 and 9 made of injected polypropylene.

Figure 1:
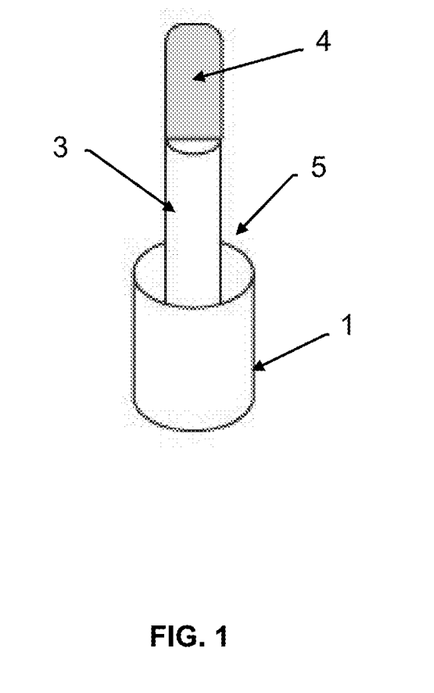
FIG. 1 shows a schematic view of the cap of the carrier container of a semi self-contained biological indicator, which in a preferred embodiment of the invention the cap 1 of the carrier container 2 comprises means 3 to hold the carrier 4 in its inner space 5.
Figure 2:
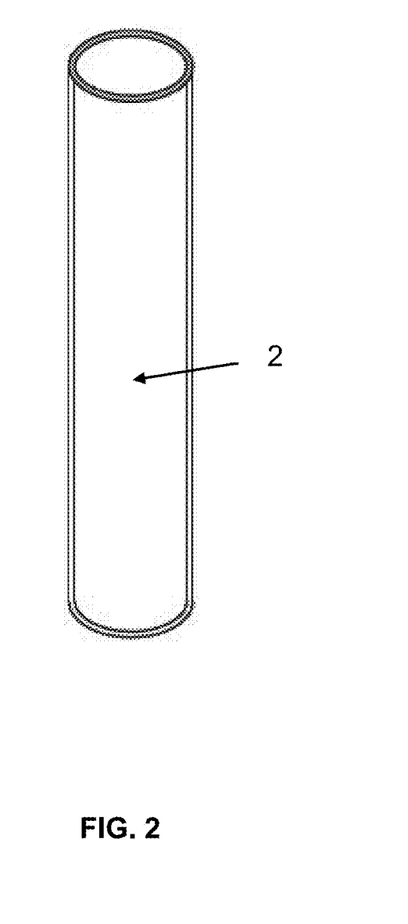
FIG. 2 shows a view of the carrier container of a semi self-contained biological indicator, which in this preferred embodiment is shaped as a tube.

As can be seen in FIGS. 1 and 2, the first container 2 has a cap 1 with fastener means 3 adapted to receive a carrier 4. In this example, such carrier 4 is a stainless steel 316 sheet and the fastener means 3 are slots in the inner part 5 of the cap 1. The configuration of these slots enables said carrier to fit inside the container when it is closed with the cap. The carrier is inoculated, on both faces of the sheet, with a suspension of *Geobacillus stearothermophilus* ATCC 7953 spores and it is allowed to dry so that spores are well adhered to the surface. This operation is performed in a sterile room so as to achieve a count of at least $1.10^6$ UFC in the carrier. Prior to the inoculation operation, materials are assembled and sterilized with ethylene oxide 600 mg/L during 2 hours.

Figure 3:
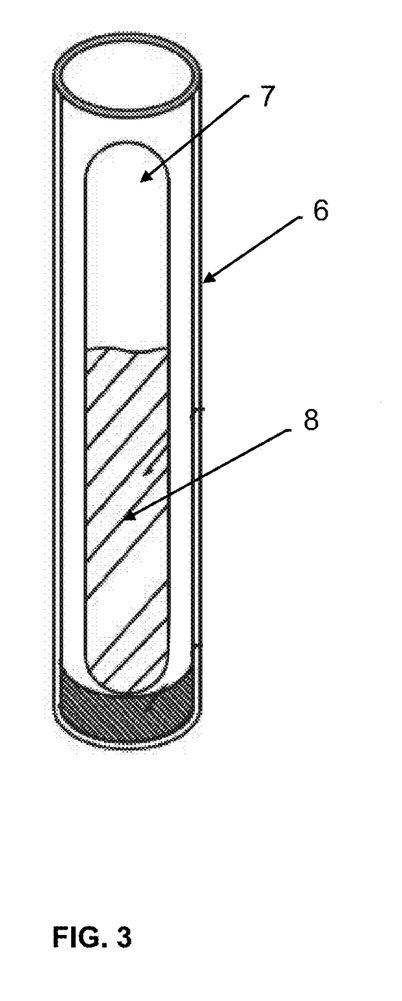
FIG. 3 shows a schematic view of a growth medium container 6 of a semi self-contained biological indicator containing a collapsible ampoule 7 with growth medium 8.
Figure 4:
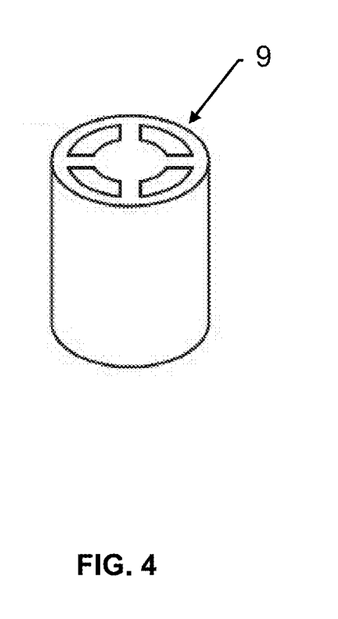
FIG. 4 shows a schematic view of the cap 9 of the growth medium container.

As can be seen in FIG. 3, the second container 6, contains an ampoule 7 made of a fragile and breakable material, preferably glass, which contains 0.7 ml of growth medium 8. This growth medium 8 comprises 0.03 g/L of bromocresol purple as chemical indicator that is able to change its color in order to identify microorganism growth; 4-methylumbel-liferyl-alpha-D-Glucopyranoside by Sigma Aldrich (San Luis, Mo., USA) as fluorescent component; 1 g/L of bacteriological peptone; 1 g/L of yeast extract; 0.5 g/L of L-valine and pH is adjusted to 7.5 with sodium hydroxide. In addition to ampoule 7, the second tube 6 contains a nonwoven polypropylene filter in its lower part to keep the ampoule in place. As in the case of the first container, the materials are sterilized with ethylene oxide 600 mg/L during 2 hours and assembled under sterile conditions.

Example 2. Method to Determine the Efficacy of a Closed Environment or Confined Space Sterilization or Disinfection Process Sterilization or disinfection assays were run in a 60 m³ room, filled with office articles, using a hydrogen peroxide vapor phase generator device (see tables below for further results). Before starting the sterilization or disinfection cycle, the cap 1 of the first tube of Example 1 containing the spores of *Geobacillus stearothermophilus* ATCC 7953 was opened and placed with the carrier 4 exposed upwards or horizontally, whether placing the cap base on a horizontal surface or else introducing the cap base into a cap-holder presenting a slot where said cap fits, like that shown in FIG. 7. The second tube may also be placed on said cap-holder or on the horizontal surface of the room to be disinfected. Subsequently, disinfection process is performed using hydrogen peroxide as a sterilizer agent. Once the process is complete, the cap 9 of the second tube is removed, the collapsible ampoule 7 is pressed so as to release the growth medium 8 and the cap 1 of the first tube—which contains the carrier 4 with spores—is taken to be inserted into, and close, the second tube 6.

In order to determine the success of the sterilization or disinfection cycle, the second container 6, closed with the cap 1 of the first container 2, is subjected to an incubation process. Said process consists in introducing said container 6 into an incubator so that it is subjected to a temperature of 60° C. for 48 hours and irradiating led light at 375 nm. The incubator is able to read the fluorescence from the tube, at a wavelength of 445-454 nm.

If the spores were not completely eliminated, upon incubation the enzyme alpha-glycosidase reacts with the fluorescent component specified in Example 1. This component does not present any fluorescence until it reacts with enzyme alpha-glycosidase which is found on the surface of the spores. After the reaction, compound 4-methylumbelliferone is released and is capable of being read by fluorescence incubators detecting a positive signal at the wavelength mentioned above. In the case of positive reading in a time period of less than 1 hour (see Table I), it can be concluded that the disinfection process was unsuccessful. On the other hand, the microbial growth resulting from the survival of spores and incubation at 60° C., allows a second visual confirmation after 48 hours. Said confirmation is given by the change in color of the ampoule, which turns from original purple into yellow.

When the fluorescence signal is negative in the course of an hour, it can be concluded that the disinfection cycle was successful. The present invention further comprises a confirmation step following incubation for 48 hours during which the medium keeps its original purple color.

Example 3. Manufacturing a Semi Self-Contained Enzymatic Biological Indicator of the Invention Like in Example 1, and referring to FIGS. 1 to 4 the semi self-contained biological indicator for determining the efficacy of disinfection processes for closed environments and confined spaces of the present example is constituted by two containers, which are respective tubes 2 and 6 with respective caps 1 and 9 made of injected polypropylene.

The first container 2 has a cap 1 with fastener means 3 adapted to receive a carrier 4. In this particular case, such carrier 4 is a metal sheet, preferably stainless steel 316 and the fastening means 3 are slots in the inner part of cap 5. The configuration of these slots enables said carrier 4 to fit inside the container 2 that is closed with the cap 1. The carrier 4 is inoculated, on both faces, with a solution of *Bacillus stearothermophilus* alpha-glycosidase provided by Sigma Aldrich (San Luis, Mo., USA) and it is allowed to dry so the enzyme is well adhered to the surface. This operation is performed in a sterile room so as to achieve a concentration of at least 50 mg of enzyme in the carrier. Prior to the inoculation operation, materials are assembled and sterilized with ethylene oxide 600 mg/L during 2 hours.

The second container 6 contains an ampoule 7 made of a fragile and breakable material, preferably glass, which contains 0.7 ml of reaction medium. This reaction medium comprises 0.2 g/l of TRIS base; 0.1 g/l of NaCl; 0.03 g/L bromocresol purple as colorant compound; 4-methylumbelliferyl-alpha-D-glucopyranoside by Sigma Aldrich (San Luis, Mo., USA) as fluorescent component and pH is adjusted to 7.5 with sodium hydroxide. In addition to the ampoule 7, the second tube 6 contains filters in its lower part to keep the ampoule in place. As in the case of the first container 2, the materials are sterilized with ethylene oxide 600 mg/L during 2 hours and assembled under sterile conditions.

Example 4. Method to Determine the Efficacy of a Closed Environment or Confined Space Sterilization or Disinfection Process Sterilization or disinfection assays were run in a 60 m³ room, filled with office articles, using a hydrogen peroxide vapor phase generator device (see tables below for further results). Before starting the sterilization or disinfection cycle, the cap 1 of the first tube 2 of Example 3 was opened and placed with the carrier 4 exposed upwards or horizontally, whether placing the cap base on a horizontal surface or else introducing the cap base into the cap-holder presenting a slot where said cap fits, like the one shown in FIG. 7. The second tube 6 may also be placed on said cap-holder or on the horizontal surface of the room to be disinfected. Subsequently, the sterilization or disinfection process is performed using hydrogen peroxide as a sterilizer agent. Once the process is complete, the cap 9 of the second tube 6 is removed, the collapsible ampoule 7 is pressed so as to release the growth medium 8 and the cap 1 of the first tube 2—which contains the carrier 4 with enzymes—is taken to be inserted into, and close, the second tube 2.

In order to determine the success of the disinfection cycle, the second container 6, closed with the cap 1 of the first container 2 is subjected to an incubation process. Said process consists in introducing said container 2 into an incubator so that it is subjected to a temperature of 60° C. and irradiating LED light at 375 nm during 1 hour. The incubator is able to read the fluorescence from the tube, at a wavelength of 445-454 nm.

If enzymes were not completely inactivated in the sterilization or disinfection process, upon incubation, the enzyme alpha-glycosidase reacts with the fluorescent component specified in Example 3. This component does not present fluorescence until it reacts with enzyme. After the reaction, compound 4-methylumbelliferone is released and it is capable of being read by fluorescence incubators detecting a positive signal at the wavelength mentioned above, in 1 hour. In the case of positive reading in a time period less than 1 hour (see Table II), it is possible to conclude that the disinfection process was unsuccessful.

When the fluorescence signal is negative in the course of one hour, it can be concluded that the disinfection cycle was successful.

Example 5. Manufacturing a Self-Contained Biological Indicator of the Invention

Figure 5:
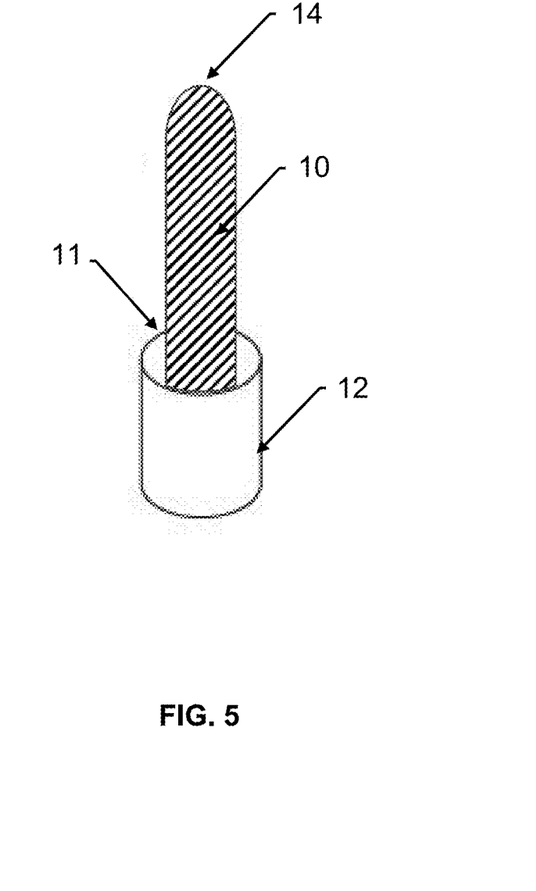
FIG. 5 shows a schematic view of another embodiment of the invention. This embodiment corresponds to a self-contained biological indicator, i.e. single container indicator, in which an ampoule 10 with growth medium is linked to the inner space 11 of a cap 12 of a carrier container 13 and the external surface 14 of the ampoule is the carrier to which the biological material is adhered.
Figure 6:
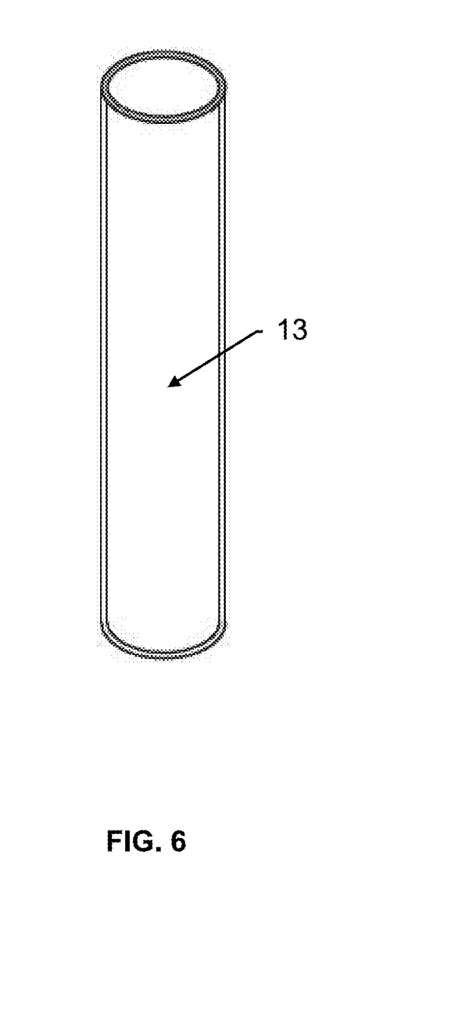
FIG. 6 shows a schematic view of the single container 13 of a self-contained biological indicator. As an alternative, the spores could also be located in the bottom of this container instead of outside of the ampoule.
Figure 7:
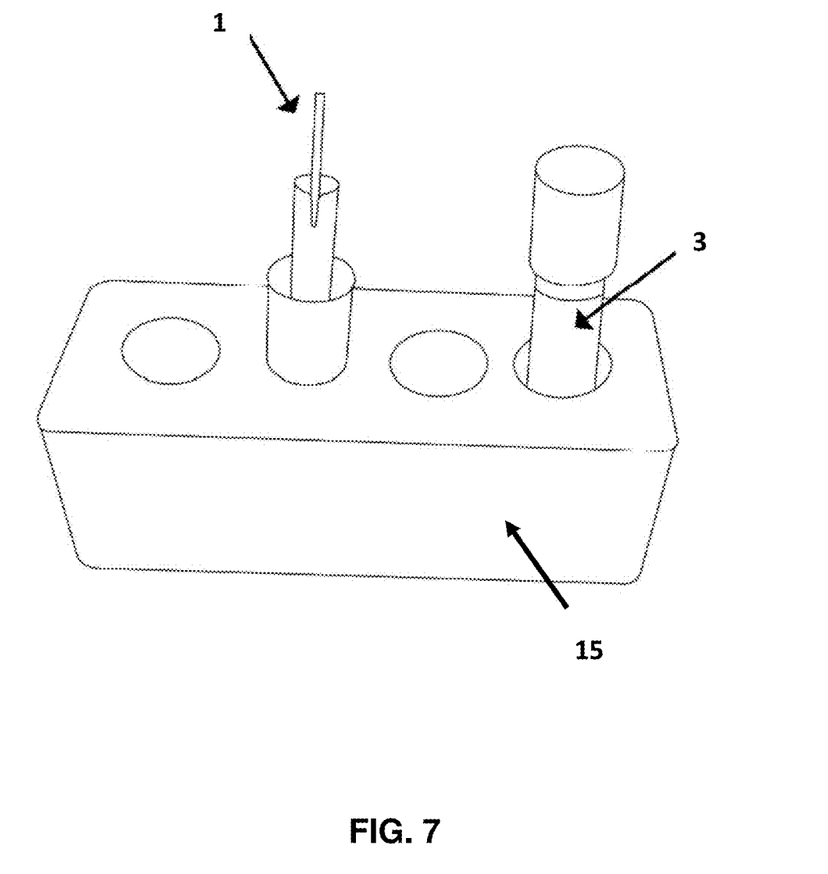
FIG. 7 shows a view of a cap-holder 15 that can hold caps 1 and tubes 3, in a preferred embodiment of the containers of the invention.
Figure 8:
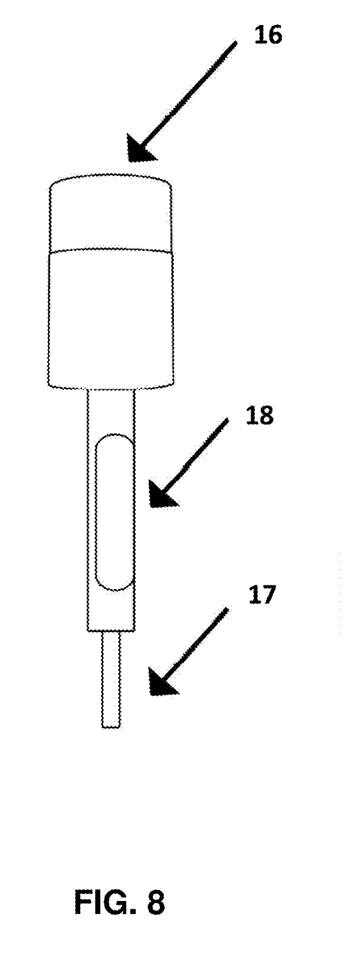
FIG. 8 shows a schematic view of the cap 16 of a self-contained biological indicator. This cap comprises a carrier of biological material 17 and an ampoule with the growth medium 8. Said ampoule fits in the inner 18 space of said cap.
Figure 9:
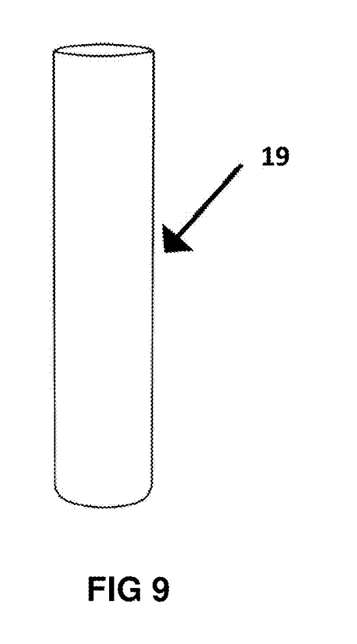
FIG. 9 shows a schematic view of the single container 19 of the self-contained biological indicator of FIG. 8.
Figure 10:
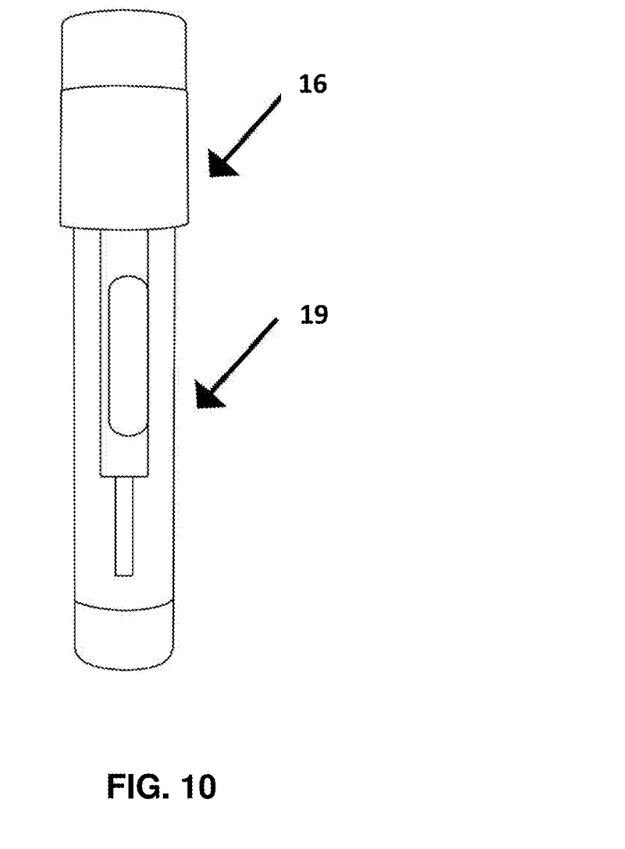
FIG. 10 shows a schematic view of an embodiment of a self-contained biological indicator of the invention. A cap 16 fits and closes the container 19 that, in this preferred embodiment, is flexible and allows breaking the ampoule in order to bring the biological material and the growth medium into contact.

Referring now to FIGS. 5 and 6, an exemplary self-contained biological indicator for determining the efficacy of sterilization or disinfection processes for closed environments and confined spaces is constituted by a single container, which in this example is a tube 13 with a cap 12 made of injected polypropylene.

The container 13 has a cap 12 with fasteners adapted to receive a carrier 14. In this example, such carrier 14 is an ampoule 10 made of a fragile and breakable material, preferably glass, which contains 0.7 ml of growth medium. This growth medium comprises 0.03 g/L bromocresol purple as chemical indicator that is able to change its color in order to identify microorganism development; 4-methylumbelliferyl beta-D-glucopyranoside by Sigma Aldrich (San Louis, Mo., USA) as fluorescent component; 1 g/L bacteriological peptone; 1 g/L yeast extract; 0.5 g/L L-valine; and pH is adjusted to 7.5 with sodium hydroxide. In addition to the ampoule 10, the tube contains filters (not shown) in its lower part to keep the ampoule in place. The materials are sterilized with ethylene oxide 600 mg/L during 2 hours and assembled under sterile conditions.

The configuration of the cap 12 enables the carrier 14 to fit inside the container 13 that is closed with the cap 12. In this embodiment the inside part 11 of the cap 12 has a hole where the ampoule 10 fits under pressure. The carrier ampoule 10-14 is inoculated on its external face with a solution of *Bacillus atrophaeus* ATCC9372 spores and it is allowed to dry so that spores are well adhered to the surface. This operation is performed in a sterile room so as to achieve a count of at least $1.10^6$ UFC in each carrier. Prior to the inoculation operation, materials are assembled and sterilized with ethylene oxide 600 mg/L during 2 hours.

Example 6. Method to Determine the Efficacy of a Closed Environment or Confined Space Disinfection Process Sterilization or disinfection assays were run in a 60 m³ room, filled with office articles, using a hydrogen peroxide vapor phase generator device (see table below for further results). Before starting the sterilization or disinfection cycle, the cap 12 of the tube 13 of Example 5 was opened and placed with the carrier 14 exposed upwards or horizontally, whether placing the cap base on a horizontal surface or else introducing the cap base into the cap-holder presenting a slot where said cap fits, like the one shown in FIG. 7. Subsequently, the disinfection process is performed using hydrogen peroxide as a sterilizer agent. Once the process is complete, the cap 12 of the tube 13 with the ampoule carrier 10-14 is taken out of the cap-holder and the container tube 13 is closed. Then the tube 13 is pressed so as to break the ampoule and release the culture medium.

In order to determine the success of the disinfection cycle, the container 13, closed with the cap 12, is subjected to an incubation process. Said process consists in introducing the container 13 into an incubator so that it is subjected to a temperature of 37° C. for 48 hours. The incubator is able to read the fluorescence from the tube, at a wavelength of 445-454 nm.

If spores were not completely eliminated, upon incubation the enzyme beta glycosidase reacts with the fluorescent component specified in Example 5. This component does not present fluorescence until it reacts with enzyme beta-glycosidase which is found on the surface of the spores. After the reaction, compound 4-methylumbelliferone is released and it is capable of being read by fluorescence incubators detecting a positive signal at the wavelength mentioned above, in 1 hour. In the case of positive reading in a time period less than 1 hour (see Table III), it is possible to state that the disinfection process was unsuccessful. On the other hand, the microbial growth resulting from the survival of spores and incubation at growth optimum temperature, allows a second visual confirmation after 48 hours. Said confirmation is given by the change in color of the ampoule, which turns from original purple into yellow.

When the fluorescence signal is negative in the course of an hour (see Table III), it can be concluded that the disinfection cycle was successful. The present invention further comprises a confirmation step following the incubation for 48 hours during which the medium keeps its original purple color.

Example 7. Manufacturing a Self-Contained Biological Indicator of the Invention

Figures 11, 12:
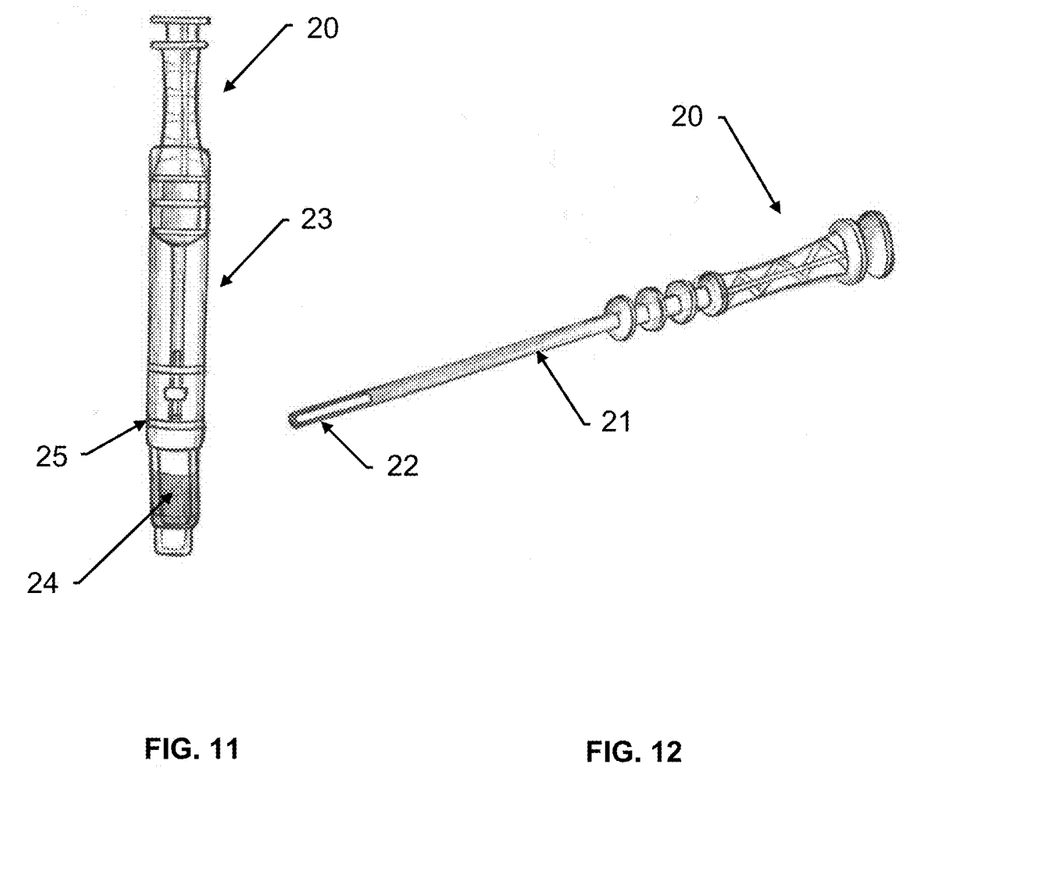
FIGS. 11 and 12 show a schematic view of an embodiment of the invention. This embodiment is a self-contained biological indicator. A cap 20 comprises in its inner space 21 a carrier 22 with biological material, and a container 23 that comprises growth medium in the bottom 24 covered by a membrane 25, which represents the collapsible ampoule of this embodiment of the invention. When the cap has been exposed to a procedure of disinfection, it is inserted in the container 23 breaking said membrane and contacting the carrier and the growth medium in the bottom.

Referring now to FIGS. 11 and 12, an exemplary self-contained biological indicator for determining the efficacy of sterilization or disinfection processes for closed environments and confined spaces is constituted by only one container, which in this example is a tube 23 with a cap 20 made of injected polypropylene. The cap 20 comprises in its inner space 21 a carrier 22 with biological material, and the container 23 comprises growth medium 24 in the bottom that is enclosed by a polypropylene film membrane 25.

This container has a cap 20 with fasteners adapted to receive a carrier 22. In this example, such carrier 22 is a cylindrical metal piece made of stainless steel, in which the biological material is inoculated.

The bottom of the container comprises the growth medium 24 enclosed by a membrane 25, which contains 0.7 ml of growth medium 24. This growth medium 24 comprises 0.03 g/L bromocresol purple as chemical indicator that is able to change its color in order to identify microorganism development; 4-methylumbelliferyl beta-D-glucopyranoside by Sigma Aldrich (San Louis, Mo., USA) as fluorescent component; 1 g/L bacteriological peptone; 1 g/L yeast extract; 0.5 g/L L-valine; and pH is adjusted to 7.5 with sodium hydroxide. The materials are sterilized with ethylene oxide 600 mg/L during 2 hours and assembled under sterile conditions.

The configuration of the cap 20 enables the carrier 22 to fit inside the container 23 that is closed with the cap 20. In this embodiment, the inner part 21 of the cap 20 has an extension of metal, i.e. carrier 22, that is inoculated with biological material. The carrier 22 is inoculated, on their external face, with a solution of *Bacillus subtilis* ATCC35021 spores and it is allowed to dry so that spores are well adhered to the surface. This operation is performed in a sterile room so as to achieve a count of at least $1.10^6$ UFC in each carrier. Prior to the inoculation operation, materials are assembled and sterilized with ethylene oxide 600 mg/L during 2 hours.

Example 8. Method to Determine the Efficacy of a Closed Environment or Confined Space Sterilization or Disinfection Process Sterilization and disinfection assays were run in a 60 m³ room, filled with office articles, using a hydrogen peroxide vapor phase generator device (see tables below for further results). Before starting the sterilization or disinfection cycle, the cap 20 of the tube 23 of Example 7 was opened and placed with the carrier 22 exposed upwards or horizontally, whether placing the cap base on a horizontal surface or else introducing the cap base into the cap-holder presenting a slot where said cap fits, like the one shown in FIG. 7. Subsequently, the disinfection process is performed using hydrogen peroxide as a sterilizer agent. Once the process is complete, the cap 20 of the tube 23 with the carrier 22 is taken out of the cap-holder and the container 23 is closed. Then the carrier 22 of the cap 20 is pressed so as to break the membrane 25 and put the growth medium in contact with the biological material.

In order to determine the success of the sterilization or disinfection cycle, the container 23, closed with the cap 20, is subjected to an incubation process. Said process consists in introducing said container 23 into an incubator so that it is subjected to a temperature of 37° C. for 48 hours. The incubator is able to read the fluorescence from the tube, at a wavelength of 445-454 nm.

If spores were not completely eliminated, upon incubation the enzyme beta-glycosidase reacts with the fluorescent component specified in Example 7. This component does not present fluorescence until it reacts with enzyme beta-glycosidase which is found on the surface of the spores. After the reaction, compound 4-methylumbelliferone is released and it is capable of being read by fluorescence incubators detecting a positive signal at the wavelength mentioned above, in less than 1 hour. In the case of positive reading in a time period less than 1 hour, it is possible to conclude that the disinfection process was unsuccessful. On the other hand, the microbial growth resulting from the survival of spores and incubation at growth optimum temperature, allows a second visual confirmation after 48 hours. Said confirmation is given by the change in color of the ampoule, which turns from original purple into yellow.

When the fluorescence signal is negative in the course of an hour, it can be concluded that the disinfection cycle was successful. The present invention further comprises a confirmation step following the incubation for 48 hours during which the medium keeps its original purple color.

Example 9. Reliability of the Biological Indicator of Example 1 of the Present Invention Several tests have been made in order to determine the reliability of the present invention. The disinfection assays were run in a 60 m$^3$ room filled with office articles. A hydrogen peroxide vapor phase generator device was used and set up considering 60 m$^3$ and 180 m$^3$ as the room volume. 30 semi self-contained biological indicators of Example 1 inoculated with 1.10$^6$ UFC of *Geobacillus stearothermophillus* ATCC 7953 spores were tested, located as far as possible from the disinfection device. Fluorescence was measured within the first hour and the results were confirmed by incubation during 48 hours at 60° C.

When a 60 m$^3$ volume was considered as the disinfection volume setting for the hydrogen peroxide vapor phase generator device, most of the indicators used, i.e. 26 out of 30, were positive (see Table I) by fluorescence. That means that the fluorescence average value was 5000 arbitrary units in one hour or less. The fluorescent indicators also change their color from purple to yellow. Then it can be concluded that the disinfection process failed. However, when the considered volume was 180 m$^3$, all the indicators used had no florescence signal after one hour and no color change after 48 hours of extended incubation at 60° C. Considering these last results it can be concluded that the disinfection process was successful.

TABLE I

Minimum time to detect fluorescence: 10 minutes. Maximum time: 45 minutes. Half time: 27 minutes.

| # TEST | Time of fluorescence (minutes) | Extended incubation result (color change) |
|---|---|---|
| 1 | 10 | + |
| 2 | 13 | + |
| 3 | 14 | + |
| 4 | 15 | + |
| 5 | 18 | + |
| 6 | 18 | + |
| 7 | 19 | + |
| 8 | 20 | + |
| 9 | 22 | + |
| 10 | 23 | + |
| 11 | 25 | + |
| 12 | 25 | + |
| 13 | 25 | + |
| 14 | 25 | + |
| 15 | 26 | + |
| 16 | 30 | + |
| 17 | 30 | + |
| 18 | 33 | + |
| 19 | 34 | + |
| 20 | 35 | + |
| 21 | 37 | + |
| 22 | 40 | + |
| 23 | 40 | + |
| 24 | 42 | + |
| 25 | 43 | + |
| 26 | 45 | + |
| 27 | No signal | − |
| 28 | No signal | − |
| 29 | No signal | − |
| 30 | No signal | − |

It could be observed that the positive results for sterilization or disinfection of confined spaces are visible starting from a time of fluorescence of 10 minutes. The present invention provides a method that starts detecting the failed disinfections of confined spaces from a time of fluorescence of about 10 minutes. This is a great advantage of the present invention because a decision of repeating the disinfection process under more intense conditions, if necessary, may be taken within a time range of about 10 minutes to about one hour. This decision-making possibility in shorter periods allows saving time and optimizing resources, for example in hospital management.

Example 10. Reliability of the Biological Indicator of Example 3 of the Present Invention The same test conditions as in the Example 9 were performed in order to determine the reliability of the biological indicator of Example 3 of the present invention.

30 semi self-contained enzymatic biological indicators of Example 3 inoculated with 50 mg of the alpha-glycosidase enzyme per carrier were tested. The indicators were located as far as possible from the disinfection device and the fluorescence was measured within the first hour by incubation at 60° C.

When a 60 m$^3$ volume was considered as the disinfection volume setting for the hydrogen peroxide vapor phase generator device, all of the indicators used, 30 in total, were positive by fluorescence. That means that the fluorescence average value was 5000 (arbitrary units) in one hour or less and the disinfection process failed (see Table II). However, when the considered volume was 180 m$^3$ all the indicators used had a negative fluorescence signal after one hour and no color change after 48 hours at 60° C.

TABLE II

Minimum time to detect fluorescence: 13 minutes. Maximum time: 38 minutes. Half time: 25 minutes

| # TEST | Time of fluorescence (minutes) |
|---|---|
| 1 | 13 |
| 2 | 13 |
| 3 | 14 |
| 4 | 14 |
| 5 | 14 |
| 6 | 15 |
| 7 | 16 |
| 8 | 16 |
| 9 | 17 |
| 10 | 18 |
| 11 | 18 |
| 12 | 19 |
| 13 | 21 |
| 14 | 22 |
| 15 | 22 |
| 16 | 25 |
| 17 | 30 |
| 18 | 30 |
| 19 | 30 |
| 20 | 31 |
| 21 | 31 |
| 22 | 35 |
| 23 | 36 |
| 24 | 36 |
| 25 | 36 |
| 26 | 37 |
| 27 | 38 |
| 28 | 38 |
| 29 | 38 |
| 30 | 38 |

TABLE III

Minimum time to detect fluorescence: 16 minutes. Maximum time: 30 minutes. Half Time: 29 minutes

| # TEST | Time of fluorescence (minutes) | Extended incubation result (color change) |
|---|---|---|
| 1 | 16 | + |
| 2 | 18 | + |
| 3 | 18 | + |
| 4 | 20 | + |
| 5 | 22 | + |
| 6 | 24 | + |
| 7 | 25 | + |
| 8 | 25 | + |
| 9 | 25 | + |
| 10 | 25 | + |
| 11 | 25 | + |
| 12 | 25 | + |
| 13 | 26 | + |
| 14 | 26 | + |
| 15 | 26 | + |
| 16 | 29 | + |
| 17 | 30 | + |
| 18 | 30 | + |
| 19 | 30 | + |
| 20 | 30 | + |
| 21 | No signal | − |
| 22 | No signal | − |
| 23 | No signal | − |
| 24 | No signal | − |
| 25 | No signal | − |
| 26 | No signal | − |
| 27 | No signal | − |
| 28 | No signal | − |
| 29 | No signal | − |
| 30 | No signal | − |

Example 11. Reliability of the Biological Indicator of Example 5 of the Present Invention The same test conditions as in the Example 9 were performed in order to determine the reliability of the biological indicator of Example 5 of the present invention.

30 self-contained enzymatic biological indicators of Example 5 inoculated with $1.10^6$ CFU of *Bacillus atrophaeus* ATCC9372 spores per carrier were tested. Fluorescence was measured within the first hour and the results were confirmed by incubation and the results were confirmed by incubation during 48 hours at 37° C.

When a 60 m³ volume was considered as the disinfection volume setting for the hydrogen peroxide vapor phase generator device, almost half of the indicators used, i.e. 20 out of 30, were positive by fluorescence. That means that the fluorescence average value was 5000 arbitrary units in one hour or less and the disinfection process failed (see Table III). In this example, although the species used to test the disinfection process is more sensitive than *G. stearothermophilus* used in the Example 1, it is still worthy to test the sterilization cycle. When the considered volume was 180 m³ all the indicators used had a negative florescence signal after one hour and no color change after 48 hours at 37° C.

Example 12. Reliability of the Biological Indicator of Example 7 of the Present Invention The same test conditions as in the Example 9 were performed in order to determine the reliability of the biological indicator of Example 7 of present invention.

30 semi self-contained enzymatic biological indicators of Example 7 inoculated with $1.10^6$ CFU of *Bacillus subtilis* ATCC35021 spores per carrier were tested. Fluorescence was measured within the first hour and the results were confirmed by incubation and the results were confirmed by incubation during 48 hours at 37° C.

When a 60 m³ volume was considered as the disinfection volume setting for the hydrogen peroxide vapor phase generator device, almost a third of the indicators used, i.e. 19 out of 30, were positive by fluorescence. That means that the fluorescence average value was 5000 arbitrary units in one hour or less and the disinfection process failed (see Table IV). In this example, although the species used to test the disinfection process is more sensitive than *G. stearothermophilus* used in the Example 1, it is still worthy to test the sterilization cycle. When the considered volume was 180 m³ all the indicators used had a negative florescence signal after one hour and no color change after 48 hours at 37° C.

TABLE IV

Minimum time to detect fluorescence: 20 minutes. Maximum time: 50 minutes. Half Time: 36 minutes

| # TEST | Time of fluorescence (minutes) | Extended incubation result (color change) |
|---|---|---|
| 1 | 20 | + |
| 2 | 25 | + |
| 3 | 26 | + |
| 4 | 28 | + |
| 5 | 30 | + |
| 6 | 30 | + |
| 7 | 30 | + |
| 8 | 32 | + |
| 9 | 35 | + |
| 10 | 35 | + |
| 11 | 35 | + |
| 12 | 36 | + |
| 13 | 36 | + |
| 14 | 37 | + |
| 15 | 37 | + |
| 16 | 37 | + |
| 17 | 38 | + |
| 18 | 38 | + |
| 19 | 40 | + |
| 20 | No signal | − |
| 21 | No signal | − |
| 22 | No signal | − |
| 23 | No signal | − |
| 24 | No signal | − |
| 25 | No signal | − |
| 26 | No signal | − |
| 27 | No signal | − |
| 28 | No signal | − |
| 29 | No signal | − |
| 30 | No signal | − |

It is also to be understood that the above description is intended to be illustrative and not restrictive. Many embodiments will be apparent to those skilled in the art upon reviewing the above description. The scope of the invention should therefore, be determined not with reference to the above description, but should instead be determined with reference to the appended claims, along with the full scope of equivalents to which such claims are entitled. Those skilled in the art will recognize, or will be able to ascertain using no more than routine experimentation, many equivalents to the specific embodiments of the invention described. Such equivalents are intended to be encompassed by the following claims.

Terms and phrases used in this application, and variations thereof, especially in the appended claims, unless otherwise expressly stated, should be construed as open ended as opposed to limiting. As examples of the foregoing, the terms "including", "comprising" or "containing" and variations thereof should be read to mean "including, without limitation," "including but not limited to," or the like. The use of terms like "preferably" or "preferred" and words of similar meaning should not be understood as implying that certain features are critical, essential, or even important to the structure or function of the invention, but instead as merely intended to highlight alternative or additional features that may or may not be utilized in a particular embodiment of the invention. The indefinite article "a" or "an" does not exclude a plurality.

The invention claimed is:

1. A biological indicator for testing the efficacy of sterilization or disinfection processes of closed environments or confined spaces, the biological indicator comprising:
   a) a carrier;
   b) a biological material supported on or embedded in the carrier; and
   c) a carrier container comprising a body and a cap;
   wherein the carrier is fixed within an inner space of the cap, the cap is able to be placed in an open position completely exposing the carrier and the biological material to the closed environment or confined space to be disinfected.

2. The biological indicator of claim 1, further comprising a cap holder for keeping the cap in the open position and exposing the carrier and the biological material to the close environment or confines space to be disinfected.

3. The biological indicator of claim 1, wherein the cap comprises an external wall with a flat portion that enables the cap placement on a flat surface in the open position.

4. The biological indicator of claim 1, wherein the carrier is made of a material selected from the group consisting of steel, polymeric materials, thermoplastic materials, synthetic or natural fibers, cellulose, vitreous materials and combinations thereof.

5. The biological indicator of claim 1, wherein the carrier comprises the biological material adhered to its surface.

6. The biological indicator of claim 1, wherein the biological material is selected from the group consisting of bacteria, spores, enzymes and combinations thereof.

7. The biological indicator of claim 6, wherein the biological material is selected from the group consisting of *Bacillus subtilis* spp., *Geobacillus stearothermophilus* spp., *Bacillus atrophaeus* spp., *Bacillus pumilus* spp., *Clostridium* spp., *Neurospora* spp., *Candida* spp. and combinations thereof.

8. The biological indicator of claim 7, wherein the biological material is selected from the group consisting of *Bacillus subtilis* ATCC35021, *Geobacillus stearothermophilus* ATCC7953, *Bacillus atrophaeus* ATCC9372, *Bacillus pumilus* ATCC27142.

9. The biological indicator of claim 1, further comprising a growth medium container that contains a growth medium for the biological material.

10. The biological indicator of claim 9, wherein the biological indicator is semi self-contained and the growth medium is contained within a collapsible ampoule which is placed within the growth medium container.

11. The biological indicator of claim 10, wherein the collapsible ampoule is a container comprising a breakable membrane.

12. The biological indicator of claim 9, wherein the growth medium container that contains the growth medium comprises an air-tight cap or a cap with a biological barrier.

13. The biological indicator of claim 9, wherein the growth medium comprises nutrients; fluorescent components which react in the presence of active enzymes by fluorescence signal; and a chemical indicator to produce a color change with a growth of microorganisms.

14. The biological indicator of claim 13, wherein the nutrients are selected from the group consisting of peptone, yeast extract, amino acids, meat extract, casein digest, tryptone, peptone from casein, soybean protein digest and combinations thereof.

15. The biological indicator of claim 9, wherein the growth medium container is an ampoule, an external surface of which is the biological material carrier.

16. The biological indicator of claim 15, wherein the ampoule is structurally linked to an internal part of the carrier container.

17. The biological indicator of claim 15, wherein the ampoule is structurally linked to the inner space of the cap of the carrier container.

18. The biological indicator of claim 9, wherein the biological indicator is semi self-contained and comprises a second container comprising a collapsible ampoule containing the growth medium; and the carrier comprises a sheet containing the biological material adhered to its surface, where the biological material is selected from the group comprising bacteria, spores and enzymes; wherein the carrier is linked to the inner space of the cap of the carrier container which, when opened, enables the positioning of the carrier completely exposed to the closed environment or confined space to be disinfected, fitted into a cap-holder, into which the cap fits.

* * * * *